United States Patent [19]

Scribner

[11] Patent Number: 5,116,386

[45] Date of Patent: May 26, 1992

[54] HAND PROSTHESIS

[76] Inventor: Albert W. Scribner, 6 Country Club Rd., Darien, Conn. 06820

[21] Appl. No.: 656,284

[22] Filed: Feb. 15, 1991

[51] Int. Cl.⁵ ............................................. A61F 2/56
[52] U.S. Cl. ..................................... 623/64; 623/57; 294/902
[58] Field of Search ............... 623/64, 65, 57; 294/26, 294/86.26, 86.27, 86.31, 87.22, 101, 902; 901/41, 45

[56] References Cited

U.S. PATENT DOCUMENTS

| | | | |
|---|---|---|---|
| 1,323,671 | 12/1919 | Baehr | 623/65 X |
| 1,421,322 | 6/1922 | Thiele | 623/64 |
| 2,226,789 | 12/1940 | Tupy | 294/902 X |
| 3,322,455 | 5/1967 | Gressbach | 294/902 X |
| 4,332,038 | 6/1982 | Freeland | 623/64 |

FOREIGN PATENT DOCUMENTS

| | | | |
|---|---|---|---|
| 0383951 | 11/1923 | Fed. Rep. of Germany | 294/902 |
| 2469917 | 6/1981 | France | 623/64 |
| 1463689 | 3/1989 | U.S.S.R. | 294/902 |

Primary Examiner—Randall L. Green
Assistant Examiner—David H. Willse

[57] ABSTRACT

This invention relates to an improved construction and arrangement for a hand prosthesis wherein cooperating finger-like and thumb-like units are adapted to be yieldably biased towards a closed condition and are capable of being opened simply by pressing the prosthesis against an external object for reception of an item to be held. In operation one or both of the finger and/or thumb-like units are adapted to conform to the general profile of the contacted surfaces of the item to be grasped. Further a normally inoperative supplemental gripping force generating means is provided which is capable, when actuated, of applying a large separate additional gripping force over and above that which is normally applied by the said yieldable biasing action. Also one of said units is adapted to be selectively positioned in at least two different fixed positions relative to the other unit in order to make possible the gripping of different ranges of sizes of items to be held.

12 Claims, 2 Drawing Sheets

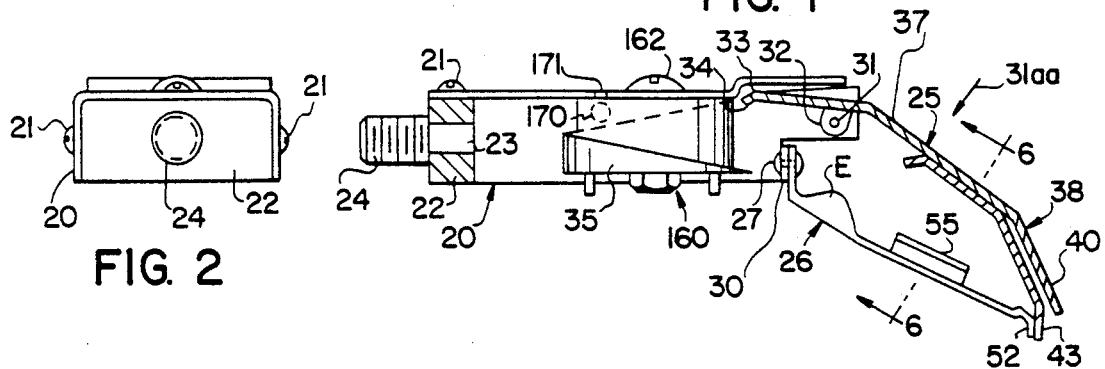
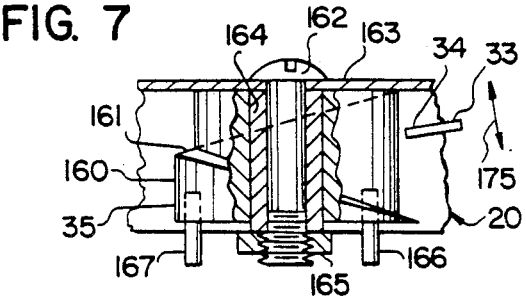
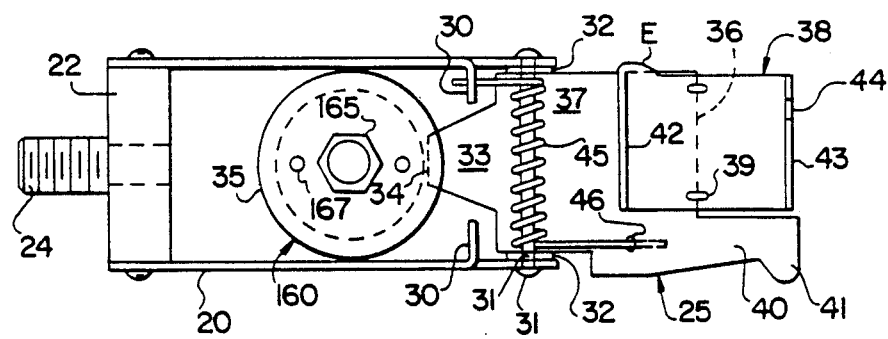

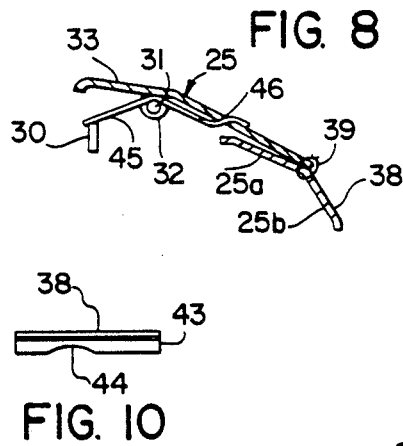
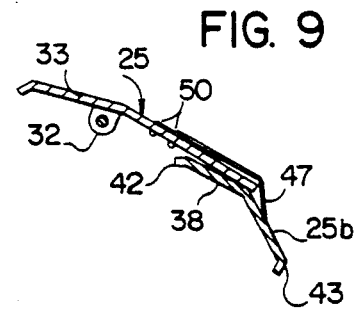
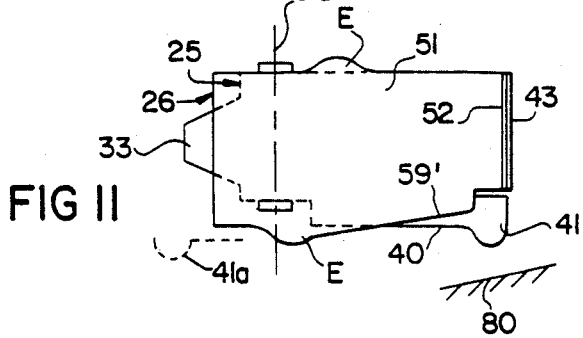
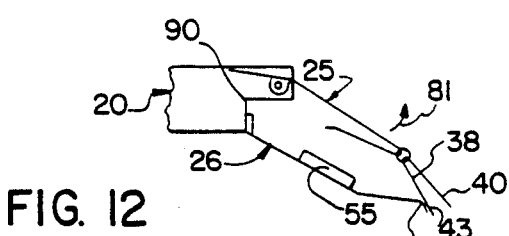
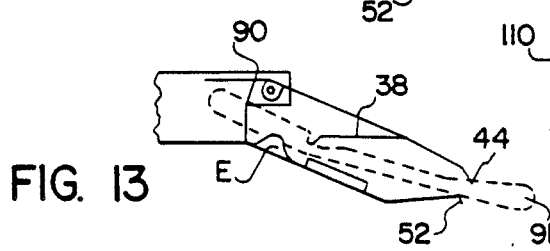
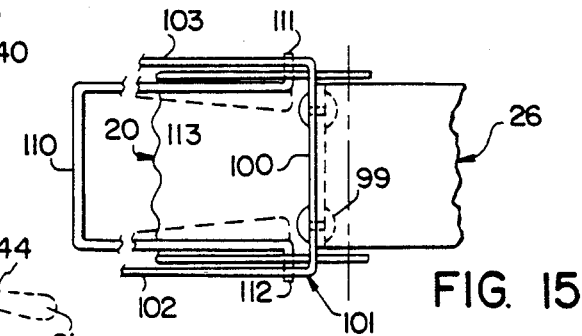
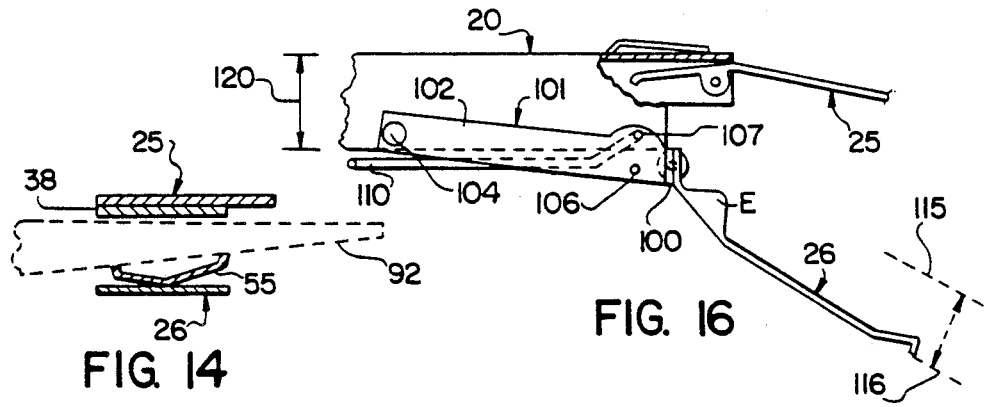

HAND PROSTHESIS

BACKGROUND OF THE INVENTION

The prior art presents at least four general types of hand prostheses; a first being the passive type which affords a close approximation of the appearance of a hand but which has no functioning mechanical parts by which any meaningful holding or manipulative activity may be performed. A second type includes those devices which have mechanically functioning parts such as hooks and the like but which have little or no aesthetic appeal. A third type includes those prosthetic devices that attempt to duplicate the specific physical construction of the natural hand and thus require a great deal of complicated mechanical finger/thumb skeletal type parts and connections therefor, and also an associated complex assortment of actuating means therefor. This third type as well as the above noted second type usually require shoulder harnesses or other similar body-powered mechanical means for actuation thereof. A fourth type of prosthesis includes the more recent myoelectric devices which include not only the usual mechanical hand parts but also very elaborate and/or expensive electrical operating and control systems. Each of the above noted types of hand prosthesis has its own set of advantages but each such type also has some inherent disadvantages that act to severely detract from its practicality. Specifically, the first noted type has no functional capability at all, while the second type can understandably leave the wearer with very real emotional and/or mental anguish by reason of the prosthesis' lack of any significant amount of aesthetic appeal. The noted third type of prosthesis require mechanical harnesses that are not only cumbersome to use but also require assistance to put on and take off of a wearer. Also they usually have too much mechanical "claptrap" in the attempted duplication of the finger/thumb etc. details of a natural hand structure and have even more so for the gearing such as cables, levers, linkages etc. which make up the various required actuating means for operating the many hand parts of such a prosthesis. As respects the fourth type the user must wear a battery pack and associated wiring somewhere on his body and must be exceptionally careful as to the environment in which the device is used in view of the susceptible nature of the electrical systems involved to exposure to common substances such as water, dirt, sand, etc. which readily act as operational contaminants and which can in turn necessitate very expensive repairs at a central "High-Tech" station. The initial costs here range in the many thousands of dollars which is just too expensive for most families particularly where everyday use thereof can be so restricted due to the noted environmental problems.

SUMMARY OF THE INVENTION

Anyone working in the development of a hand prosthesis soon concludes that any such prosthesis, including the one disclosed herein, can match only a pitiful few of the capabilities of the human hand. About the best that can be hoped for from a practical stand point here is the provision of a device and/or system that is mechanically simple, durable, relatively inexpensive, aesthetically acceptable, may be readily repaired, and finally is able to afford a few carefully selected object holding capabilities to assist to some extent in the carrying out of a few of the wearer's more common daily type tasks. The present invention seeks to provide a prosthesis which meets at least some aspects of each of the several above noted desired attributes while at the same time avoiding any of the major disadvantages of the four general types of prostheses noted above. In the area of performance capabilities this invention emphasizes the hand holding function as opposed to hand manipulative functions; the latter being illustrated by activities such as picking up small objects or where the object being handled might have to be moved about by and relative to the hand prosthesis itself. Such manipulative activity can best be performed by the one natural hand that the wearer of the present prosthesis presumably has. The article holding capabilities with which the present invention is primarily concerned are three in number. The first item holding mode contemplated here is to make possible the holding of objects in the manner that one normally holds a pencil or a spoon. This holding mode is common to many hand tasks and is very helpful when it can be performed with relative ease and with a firmness of grip. The second mode of holding an object that is of particular concern here is that which might be referred to as "handle" mode. This mode is essentially that which a person would normally use to hold the handle of an article such as a hammer or a tennis racket etc. where the handle portion of the object passes over the palm of the hand with the thumb and fingers wrapped around opposite sides of the object handle. A prosthesis having reasonable degree of proficiency in performing this second type of holding mode would be very helpful where heavier objects or loads are to be encountered. The third object holding mode can be referred to as the fingertip mode whereby small objects and sheet type material may be delicately held. In these three holding modes it is highly desirable that a hand prosthesis be able, in its gripping action, to at least in part conform itself to the shape of the engaged portions of the item being held and this operational characteristic is to a fair degree met by the capability of the present prosthesis.

The present invention seeks to eliminate the need for prosthesis actuating shoulder harnesses with their attendant bowden wire type linkages and other displacement producing mechanisms that are normally used to open or otherwise actuate the gripping means of the prosthesis. Rather here the hand portion of the prosthesis is provided with a simple contact element which the wearer can press against any external object or surface and thereby open the prosthetic gripping means so as to permit the latter to receive an article to be held. This greatly simplifies the apparatus needed to operate the prosthetic device.

The instant invention also makes possible the varying of the gripping force with which objects may be held; lower forces for lighter objects and higher forces for heavier items or for an article that might need to be held tighter than usual.

Additional structural and functional features and capabilities of the present prosthesis, such as ease of "in the field" maintenance and/or repair and replacement of parts, will be shown in and seen from the following detailed disclosure.

EXPLANATION OF THE DRAWINGS

FIG. 1 is a front elevational view in partial section of the present hand prosthesis and shows the general organization of the main portions of the present invention.

FIG. 2 is a view of the left, as seen in FIG. 1, end of the present prosthesis.

FIG. 3 is a top view of a portion of the finger-like jaw unit as seen in the direction of arrow 31aa shown in FIG. 1.

FIG. 4 is an underside view of the apparatus of FIG. 1 with the lower thumb-like jaw unit 26 removed so as to expose, inter alia, the construction and arrangement of the underside of the finger unit 25.

FIG. 5 is a plan view showing the upper inside face of the fixed thumb-like jaw unit 26 as viewed in the direction indicated by the said arrow 31aa of FIG. 1, and with the finger-like unit 25 removed.

FIG. 6 is a sectional view taken along section line 6—6 of FIG. 1.

FIG. 7 is a detail elevation view in partial section illustrating the configuration and arrangement of the camming device for generating a supplemental gripping force.

FIG. 8 is a fragmentary sectional view illustrating the spring arrangement for normally yieldably actuating the finger-like jaw unit of the present prosthesis.

FIG. 9 is a fragmentary sectional view similar to that of FIG. 8 and illustrates the light spring arrangement for yieldably biasing the compound gripping plate of the finger-like unit to a normal clockwise position.

FIG. 10 is a fragmentary end view showing the configuration of the outer tip of the compound gripper plate of the finger unit.

FIG. 11 is a bottom, as viewed in FIG. 1, view of the finger unit and thumb unit particularly illustrating the relative overlapping of the respective outer profiles of these two units.

FIGS. 12 and 13 are diagrammatic sketches illustrating the functional cooperation between the thumb and finger units.

FIG. 14 is a sectional view corresponding to that of FIG. 6 and illustrates the functional cooperation between the thumb and finger units in holding an article.

FIG. 15 is a bottom, as seen in FIG. 1, view illustrating a structural modification of the present prosthesis whereby the thumb-like unit is adapted to be secured in either of two fixed positions relative to the prosthesis frame so as to accommodate respective different ranges of sizes of items to be held.

FIG. 16 is a front elevational view of the apparatus shown in FIG. 15.

DETAILED DESCRIPTION OF THE INVENTION

Many present hand prostheses comprise three general sections or portions; namely a socket portion that is usually custom-made to receive the end of the deficient limb (this end here usually being below the elbow), a harness portion that operatively connects the socket section to the upper regions of the wearer's arm, and a terminal or hand simulating section that is detachably secured to the said socket section as for example by means of a standard sized threaded connection. The present invention deals only with the noted hand simulating portion of the overall prosthesis and for the purposes of illustrating and describing the present invention it will be assumed that the wearer requires a left hand prosthesis. As will be apparent, a corresponding mirror-image construction and operation may be used where a right hand prosthesis is required. Further the invention described herein deals only with the "hardware" of the hand simulating portion of the prosthesis and does not include or present any aspect of the external or skin covering that would certainly be applied to the present hardware in order to give the prosthesis an outward appearance of a natural hand. As the disclosure progresses it should be noted that the overall configuration of the present hardware profile has been made such that it duplicates fairly closely the overall natural hand profile or shape so that another person, observing for the most part only the back of the hand, the finger grouping, and the upper portion of the thumb area, would do so and not sense the artificiality of the hand. This outer profile duplication then makes it possible to attach to the hardware described herein an aesthetic covering of well known materials such as rubber, thermoplastics etc. which to another person gives the appearance of being very authentic. The hereinafter described prosthesis "controls" and access thereto are located on the side of the prosthesis facing the wearer's own body so as to thereby be only minimally observable.

Referring to FIGS. 1 and 2 there is shown a hand prosthesis which comprises an elongated U-shaped frame 20 that can be made from sheet metal bent into the elongated channel form illustrated in FIGS. 1 and 2. Secured by means of screws 21 to the left end, as viewed in FIG. 1, of said frame is a block 22 into which is press fitted the reduced end 23 of a threaded member 24. Member 24 is adapted to be threaded into an above noted prosthesis socket section so as to thereby detachably secure the present hand simulating section to the socket section of a full prosthesis assembly.

Pivotally mounted at the right hand end, as seen in FIG. 1, of the frame 20 is a finger-like unit 25 that is adapted to swingably cooperate with a thumb-like unit 26 that is fixedly secured by means of rivets 27 or the like to the inwardly bent off ears 30, FIGS. 1, 4 and 5, of said frame 20. For ease of referral and description the units 25 and 26 will be hereinafter referred to in this specification as the movable jaw and fixed jaw respectively; such jaws in combination defining the article gripping means for the instant prosthesis. The jaw 25 is pivotally coupled to the frame 20 by means of a pivot pin 31 which extends through the axially aligned holes in the 90 degree bent off ears 32, FIGS. 1 and 4, of the jaw 25 and through similar axially aligned holes in the side flanges at the right hand, as seen in FIG. 1, end of the said frame. The integral lever 33 extending to the left from the main body portion 37 of the jaw 25 is adapted to cooperate with a cam member 35 as will be described below. To an outer or right hand end edge 36, FIG. 3, of said body portion 37 of the jaw 25 is pivotally coupled by any suitable hinge means such as wire loops 39, FIG. 8, the center portion of a compound gripper plate 38. The jaw 25 is also provided with an outwardly extending finger projection 40, FIG. 4, having a downwardly projecting tip 41 the purpose of which will be described below. As will be apparent from FIGS. 1 and 4 the location of the finger projection 40 corresponds to that of the little finger of an actual hand. The shape of the compound gripper plate 38 is generally rectangular as may be seen from FIG. 3 and includes as best illustrated in FIGS. 8 and 9 two mutually angularly disposed central panels or sections 25a and 25b which respectively end in short further bent off inner and outer article engaging tips 42 and 43, FIG. 9. The outer tip 43 is formed with a notch 44 as is shown in FIGS. 4 and 10. The jaw 25 is yieldably biased in a clockwise direction, as seen in FIG. 1, by means of a torsion spring 45, FIG. 4, the coils of which surround said pivot pin 31; one end leg of said spring abutting any suitable adjacent portion of the frame such as one of said bent off ears 30 as shown in FIG. 8 while the other end leg of the spring extends to and passes up through a hole 46, FIGS. 4 and 8, in the main body portion 37 of jaw 25 so as to bear against the upper surface of said plate body 37 as illustrated in FIG. 8. The compound gripper plate 38 is yieldably biased in a clockwise direction as seen in FIGS. 1, 8 and 9 by any suitable means such as a small leaf spring 47, FIG. 9, the outer or right end of which bears against the said panel portion 25b, FIG. 9, of the compound gripper plate 38 while the other end thereof is fixedly secured to the said body portion 37 of jaw 25 by any suitable fastening means such as rivets 50, FIGS. 3 and 9. Spring 47 serves to bias plate 38 to a normal clockwise position determined by engagement of the panel 25a thereof with the adjacent underside surface of the jaw 25 as best seen in FIG. 8.

The fixed lower jaw 26 cooperates with the jaw 25 and includes a central portion 51, FIG. 5, and a bent off outer tip 52, FIGS. 1, 5, and 11. Pivotally carried by means of any suitable hinge means, such as wire loops 54, FIG. 5 and 6, on the surface of said central jaw portion 51 is a second compound like gripper plate 55, FIGS. 1, 5, and 6 which includes mutually angularly disposed central panels and also bent off article engaging tips 57 and 58, FIG. 6, disposed at the outer ends of said panels. As will be apparent the gripper plate 55 is capable of partaking of a rocking action as indicated by the arrow 59 of FIG. 6. If desired, any suitable light spring means not shown may be used to yieldably bias said gripper plate 55 to a normal clockwise or counter clockwise position against the inner face of the jaw 26. As is shown in the various Figures the jaws and compound plates may be provided with slightly bent off ears E where needed or desired in order to facilitate the gripping and holding of articles in any of the three hereinafter described article holding modes.

In the normal operation of the present prosthesis the manner in which the jaw 25 is moved away from its normally closed FIG. 1 position is as follows. From FIG. 11 it will be noted that the depending tip 41 of the projection 40 on the jaw 25 projects below the lower edges 59', FIG. 11, of the jaw 26 so that the prosthesis wearer can bring said tip 41 into contact with any external surface or object designated at 80 in FIG. 11 and once such contact is so made the prosthesis as a whole may be slightly displaced towards the body of the wearer, i.e. towards the observer of FIG. 11, so that the jaw 25 effectively swings away from the jaw 26 against the action of spring 45 as indicated by arrow 81 of FIG. 12. (In fact here however it is the fixed jaw 26 that is moved away from jaw 25 during this jaw opening action.) In any event the article gripping means defined by jaws 25 and 26 are thus opened so as to be able to receive an object to be held and to grip the latter under the action of said spring 45 after said contact with the said surface 80 by the tip 41 is terminated. By being thus able 40 open the jaws of the present prosthesis the need for shoulder harnesses and other similar mechanics actuating means is eliminated thereby greatly simplifying the construction and the putting on and taking off of the present prosthesis. If desired the finger projection 40 may extend to the left instead of the right of the axis 31a, FIG. 11, of the pivot pin 31 so that the location of its depending tip 41a is now located on the left side of the pin axis 31a, as is diagrammatically illustrated in FIG. 11. Under these conditions the wearer will, after said contact is made with an external surface, push the prosthesis away from himself in order to open the jaws.

FIG. 13 diagrammatically illustrates how an article is held in what will be referred to here as a "pencil" holding mode. The article shown in FIG. 13 by the dotted lines 91 is held at several points along its length, i.e. by the notch 44 at the outer end of the compound gripper plate 38, the thumb tip 52, the inner end 42 of the compound plate 38, the bent off ear E and the notch 90, FIGS. 12 and 13, existing at the right hand end portion of the frame 20. The flexibility afforded by the differential setting movement to the swivelled gripping position of the compound gripper plate 38 in contacting odd shaped articles such as 91 shown in dotted lines in FIG. 13 enables the present gripping means to efficiently grasp a wide variety of even or unevenly shaped objects to be held in this "pencil" holding mode. FIG. 14 diagrammatically illustrates how an object may be held in what will be referred to as a "handle" holding mode; i.e. how the prosthesis wearer would normally grip the handle of items such as a hammer, a tennis racket, etc. where the item handle extends over the palm and is gripped on opposite sides thereof by the thumb and fingers respectively. Here the article shown in FIG. 14 by dotted lines 92 is held at various points along its length by the lower surfaces of compound plate 38 and by the opposite ends 57 and 58, FIG. 6, of the swivelled gripper plate 55; the latter having pivotally moved so as to accommodate the irregular shape of said article 92. The ability of the compound gripper plates 38 and 55 to swivel about axes that are respectively mutually skewed enables the present fixed and movable jaw means to effectively conform to the general shapes of the widely varying contacted surfaces of articles to be held; which capability is most significant in any article holding effort by a hand prosthesis. A third mode of holding an article is illustrated in FIGS. 1 and 12. Here the mutually cooperating action of the nearly flat surfaces of the outer tips 43 and 52 respectively of the movable and fixed jaws 25 and 26 define a "finger tip" mode of holding an item that is most applicable to the gripping of small articles and/or sheet materials between said tips. The item engaging surfaces of the jaws 25 and 26 may be provided with rubber-like coatings in order to increase their frictional holding ability. Also such rubber-like surfaces may be dimpled in order to further enhance their article retention capacity; these surface features being well understood in the art.

FIGS. 1, 4, 7 and 8 best illustrate the construction of a supplemental grip force generating system 160 that is provided for the present prosthesis. In the normal course of operation of the instant prosthesis the coil spring 45 yieldably biases the jaw 25 towards a normal, FIG. 12, position wherein the outer tip 43 of the compound gripper plate 38 engages the cooperating lip surface of the tip 52 of the lower jaw 26 as illustrated in FIG. 1. When any article is held between the jaws 25 and 26 it will be gripped first by tip 43 and then additionally by the inner tip 42 with a combined force corresponding to the effective force then developed by the said coil spring 45. This effective force may be sufficient for holding many light objects but there may be instances where heavier items are to held or where grip forces greater than that afforded by the spring 45 are desired. To this end the system 160 is provided; which system is normally inactive but may be manually actuated to greatly increase the gripping force applied by the jaws 25 and 26 to the article being held. The system 160 is actuatable to generate and apply this increased force over and above the grip force then developed and applied by coil spring 45 and is capable of doing so for every gripping position of the movable jaw 25 over its entire range of gripping positions. Referring to FIGS. 1, 7 and 8, the system comprises a cam 35 having a helical ramp surface 161, FIG. 7, formed on the outer cylindrical portions thereof. The cam ramp 161 is adapted when the cam is properly rotatably positioned to cooperate with the outer tip 34 of the said integral lever 33 of the movable jaw 25. Cam 35 is rotatably mounted on frame 20 by means of a bolt 162 which extends through a suitable aperture in the upper web portion 163 of the frame 20 and passes downwardly through a tubular spacer member or sleeve 164, FIG. 7. Cam 35 which is provided with a suitable axial bore therethrough is rotatably mounted over said sleeve and a nut 165 is threaddedly secured to the lower end of bolt 162 so as to fixedly secure the sleeve to the frame. In that the axial length of sleeve 164 is slightly greater than that of the cam 35 the latter will be secured to but will be free to rotate relative to the said frame 20. A pair of pins 166 and 167, FIGS. 1, 7 and 8, press fitted into holes in the lower face of cam 35 facilitate manual rotation of said cam. In order to yieldably retain the cam 35 in a normal inactive rotative position any suitable conventional type yieldable detent means may be used such as a small spring biased ball 170, FIG. 1, which is carried adjacent the upper face of cam 35 and which engages and cooperates with a smaller diameter aperture 171 formed in the adjacent web portion of the frame 20. With the cam 35 yieldably detented in its normal inactive position illustrated in FIGS. 1 and 7 the movable jaw 25 with its rearwardly extending lever 33 is operationally free from any interference from the ramp 161 of the cam 35 and thus can swing through its full range of operative arcuate movement as indicated by arrow 175 of FIG. 7. When the jaw 25 is (a) in any given operative arcuate position and (b) is gripping an article being held under the grip force action of coil spring 45, and (c) it is then desired to have an additional higher gripping force applied to said jaw 25 the prosthesis wearer need only to use his right hand to rotate cam member 35 in a clockwise direction, as seen in FIG. 4, away from its normal yieldably detented inactive rotary position shown in FIGS. 1 and 4, and to a rotary position wherein a portion of the helical ramp 161 engages the underside of the tip 34 of said lever 33 so as to exert a degree of positive upward force on said tip as determined by the amount of torque then applied to the cam 35. The cam will functionally remain in this rotary position even when said torque is no longer applied and hence the thus generated and applied higher gripping force applied to jaw 25 will remain applied until the cam is manually rotated in a counterclockwise direction and back to its said normal position. Thus the cam 35 constitutes a very simple reliable one-piece means for generating a desired higher level of grip force.

Referring to FIG. 15 and 16, there is shown a modification of the above described prosthesis. Here the previously fixed lower jaw 26 is adjustably mounted on frame 20 so as to be positionable in more than one fixed position whereby different ranges of sizes of articles to be held may be accommodated. Here the lower jaw 26 is secured as by any suitable means such as rivets 99, FIG. 15, to the intermediate transverse portion 100 of the U-shaped lever means 101 that has two legs 102 and 103 which extend to the left, as seen in FIGS. 15 and 16, and which are pivotally connected to the side flanges of the main frame 20 by means of coaxially aligned rivets such as 104 shown in FIG. 16. The right hand ends of said legs, as seen in FIGS. 15 and 16, are each provided with a pair of spaced holes such as 106 and 107 located on a circular arc centered on said pivot rivets 104. A generally U-shaped wire detent member 110 is provided which has substantially parallel legs that are formed with coaxial 90 degree bent off ears 111, 112 respectively which are adapted to pass through the respectively associated coaxial holes in the side flanges of said frame 20 and through either of the two coaxial sets of lever holes 106 or 107. When said short wire ears 111, 112 are operatively disposed in the coaxial pair of holes 106 in said legs 102 and 103 the jaw 26 will be fixedly secured on frame 20 in the position shown in FIG. 1. When it is desired to hold an object larger than that which could normally be held by the fully open jaw means as arranged in FIG. 1, then the side legs of said U-shaped wire detent 110 are squeezed and thus flexed towards each other by the prosthesis wearer as diagrammatically indicated by the dotted lines 113 of FIG. 15 so as to thereby withdraw the ears 111, 112 from said set of coaxial holes 106 respectively formed in the lever legs 102 and 103 whereafter the jaw 26 may, be pivotally moved about the pivot axis of said rivets 104 so as to drop the jaw 26 from a normal FIG. 1 position illustrated by line 115 of FIG. 16 to a wider open fixed position illustrated by line 116 of FIG. 16 in which wider open position the said wire ears 111, 112 may snap outwardly into the coaxial set of holes 107 in said lever legs 102, 103 so as to thereby fix the said jaw 26 in said wider open position 116. The corresponding adjustment step is made to reset the jaw 26 back to its said normal position shown in FIG. 1 and illustrated at 115 of FIG. 16. With the modification shown and described in FIGS. 15 and 16 the depth dimension 120, FIG. 16, of the side flanges of the channel frame 20 may be increased slightly so as to ensure that the operation of the wire detent member 110 does not structurally interfere with the presence and/or operation of the cam 35.

It will be seen that the invention disclosed herein meets to a substantial extent each of the above noted characteristics desired for a hand prosthesis. As will be apparent, the so-called Rachael Device shown and described herein is not a "high-tech" prosthesis, nor one that is particularly directed to one specific application, or one that is so general in its gripping mode(s) that it is ineffective in any one given mode. Rather, it seeks to incorporate as many very practical physical and operational characteristics as possible including some new functional features for three specific common types of gripping modes while exhibiting none of the noted major deficiencies of the prior art devices.

What is claimed is:

1. An improved hand prosthesis: comprising
  a frame;
  gripping means carried by said frame and adapted to assume open and closed conditions; said gripping means including a thumb-like jaw means and a cooperating finger-like jaw means, one of said jaw means being movably carried by said frame for cooperating movement towards and away from the other of said jaw means;
  biasing means adapted to normally yieldably urge said movable jaw means towards said other jaw means; and actuating means for said movable jaw means, said actuating means comprising a contact element coupled to said movable jaw means and located in a position corresponding to that of the little finger of an actual hand and adapted when said hand prosthesis as a whole is moved by the wearer so that said contact element is pressed against an external object the resultant force applied to said element will displace said movable jaw means away from said other jaw means against the action of said biasing means whereby said gripping means may receive an item to be held, and when said hand prosthesis is moved so that said contact element is no longer pressed against said external object and said force is now removed from said contact element said movable jaw means will be moved to a gripping condition under the action of said biasing means whereby said gripping means may grasp and hold the item to be held.

2. Apparatus as defined by claim 1 additionally comprising:
supplemental grip force generating means mounted on said frame and adapted when actuated to apply an added grip force to said gripping means independent of the action of said biasing means whereby a larger gripping force may be applied to said item than would otherwise be normally applied thereto by just the action of said biasing means.

3. Apparatus as defined by claim 1, wherein one of said jaw means movably carries a compound gripper means whereby said movable compound gripper means in cooperation with the said other, jaw means may by differential motion engage said item to be held at more than one point and thus positionally conform to the general shape of the engaged portion of said item in response to said movable jaw means being moved to a condition gripping said item.

4. Apparatus as defined by claim 1 additionally comprising:
means for mechanically detachably connecting the hand section of the prosthesis as a unit to the upper portions of the prosthesis, there being no actuating connections between said hand and said upper portions of said prosthesis.

5. An improved hand prosthesis: comprising
a frame;
gripping means carried by said frame and adapted to be moved to open and closed conditions;
said gripping means including a thumb-like jaw means and a cooperating finger-like jaw means, one of said jaw means being movably carried by said frame so as to be capable of cooperative movement towards and away from the other of said jaw means; a first compound grip plate swingably carried by one of said jaw means for cooperation with the said other jaw means;
actuating means for moving said movable jaw means towards said other jaw means whereby when said compound swingable grip plate engages an item to be held said grip plate partakes of a differential motion in engaging said item to be held at at least two spaced apart points on said plate and thereby positionally conforms itself to the general configuration of the engaged portion of said item, such differential positioning of itself by said compound plate thus enabling items of various shapes to be efficiently gripped by said gripping means.

6. Apparatus as defined by claim 5 wherein said finger-like jaw means is pivotally connected to said frame, and wherein said first compound grip plate is pivotally connected to said finger-like jaw means; and
a second compound grip plate swingably secured to said other jaw means and adapted by swinging item engaging movement to cooperate with said one jaw means to efficiently hold items of varying shapes, the swinging axes of said compound plates being mutually skewed.

7. Apparatus as defined by claim 5; additionally comprising locking means for securing said other jaw means in a plurality of fixed positions relative to said frame so that different ranges of sizes of items to be held may be respectively accommodated by said gripping means for different fixed positions of said other jaw means.

8. Apparatus as defined by claim 5; additionally comprising supplemental grip force generating means mounted on said frame and adapted when actuated to apply a positive added grip force to said gripping means at any one of the latter's various possible operative positions whereby a larger gripping force may be applied to said item than would otherwise be applied thereto by just the normal action of said actuating means.

9. Apparatus as defined by claim 8 wherein said supplemental force generating means comprises a rotary cam having a helical ramp surface formed on the outer portions thereof.

10. An improved hand prosthesis: comprising
a frame;
item gripping means including a pair of cooperating jaw means carried by said frame and adapted to be moved to item gripping and release conditions;
actuating means for said gripping means normally applying a basic grip force to an item to be held by said gripping means; and
supplemental grip force generating means carried by said frame and being operationally independent of said actuating means and adapted when actuated to apply an added grip force to said gripping means at any one of the latter's various possible operative gripping positions whereby a larger total gripping force may be applied to said item than would otherwise be applied thereto by just the normal action of said actuating means; one of said jaw means being movably mounted on said frame and being adapted to be normally actuated by said actuating means, and said supplemental grip force generating means including a cam member which is rotatably carried by said frame and which has a helical type cam surface thereon that is adapted to engage and urge said movable jaw means towards the other of said jaw means in response to the rotation of said cam member.

11. Apparatus as defined by claim 10, wherein one of said jaw means movably carries a compound gripper means which in cooperation with the said other jaw means may by differential motion engage said item to be held at more than one point and thus positionally conform to the general shape of the engaged portions of said item in response to said movable jaw means being moved to a condition gripping said item.

12. Apparatus as defined by claim 11: additionally comprising locking means for securing said other jaw means in a plurality of fixed positions relative to said frame so that different ranges of sizes of items to be held may be respectively accommodated by said gripping means for different fixed positions of said other jaw means.

* * * * *